(12) United States Patent
Cheng et al.

(10) Patent No.: US 6,419,637 B1
(45) Date of Patent: Jul. 16, 2002

(54) FORECASTING SYSTEM FOR MENSTRUATION OF WOMEN

(75) Inventors: Weily Cheng, Hsintien; Hui-Wen Cheng, Taipei, both of (TW)

(73) Assignee: TrustMed.Com Corporation, Taipei (TW)

( * ) Notice: Subject to any disclaimer, the term of this patent is extended or adjusted under 35 U.S.C. 154(b) by 21 days.

(21) Appl. No.: 09/631,458

(22) Filed: Aug. 3, 2000

(51) Int. Cl.⁷ .............................................. A61B 10/00
(52) U.S. Cl. ....................................................... 600/551
(58) Field of Search ................................ 600/300, 551, 600/588

(56) References Cited

U.S. PATENT DOCUMENTS 5,974,124 A * 10/1999 Schlueter, Jr. et al. .. 379/106.02
6,022,323 A *  2/2000 Jackson ....................... 600/551
6,088,594 A *  7/2000 Kingdon et al. ............. 455/457

* cited by examiner

*Primary Examiner*—Kevin Shaver
*Assistant Examiner*—Pamela Wingood
(74) *Attorney, Agent, or Firm*—Wood, Phillips, Katz, Clark & Mortimer

(57) ABSTRACT

A forecasting system takes advantage of an E-mail system of the internet to forecast different days of a following menstruation period of a woman via different terminals, such as a mobile telephone which supports WAP and a personal computer which is capable of connecting with the internet. The working of the forecasting system includes entering via a terminal relative information of menstruation of a woman, establishing a data base in a data server of the internet depending on the entered information, calculating an ovulation day, impregnable days, starting and ending days of a following menstrual flow of the woman, and sending out inquired forecast information to the woman via the different terminals.

7 Claims, 4 Drawing Sheets

FORECASTING SYSTEM FOR MENSTRUATION OF WOMEN

BACKGROUND OF THE INVENTION

1. Field of the Invention

The present invention relates to a forecasting system, which takes advantage of an E-mail system of the internet or mobile phone which supports Wireless Application Protocol (WAP) to forecast via different terminals menstruation periods of a woman.

2. Description of Related Art

When female humans reach puberty, they begin menstruation, which indicates the females are capable of conception. A healthy nonpregnant woman continuously repeats her period till reaching her menopause. Menstruation is usually a disturbance for women, especially career women who may have very tight business schedules. A woman has to remember her starting day of last menses to calculate her ovulation day, impregnable days and starting and ending days of a following menstrual flow, in order to smoothly prepare for different times of a menstruation.

However, it is generally difficult for a woman to remember her starting day of last menses every time, and particularly to learn different formulas of calculation of ovulation days, impregnable days and starting and ending days of a following menstrual flow. Moreover it is much more difficult for a woman whose menstruation is irregular to remember her starting day of a last menses every time and calculate different days of a following menstruation.

Therefore, it is an objective of the invention to provide a simple, convenient and recollectable forecasting system for women to mitigate and/or obviate the aforementioned problems.

SUMMARY OF THE INVENTION

The object of the present invention is to provide a forecasting system, which takes advantage of an E-mail system of the internet to forecast via different terminals different days of a following menstruation of a woman, such as a mobile telephone which supports WAP or a personal computer which is capable of connecting with the internet. The working of the forecasting system includes entering relative information of menstruation of a woman via a terminal, establishing a data base in a data server of the internet depending on the entered information, calculating ovulation days, impregnable days, starting and ending days of a following menstrual flow of the woman, and sending out an inquired forecast information to the woman via the terminal.

The detailed features of the present invention will be apparent in the detailed description with appropriate reference to the accompanying drawings.

DETAILED DESCRIPTION OF THE PREFERRED EMBODIMENT

The present invention relates to a forecasting system used to forecast an ovulation day, impregnable days and a starting day of a following menstruation of women. The working of the forecasting system includes:

1. entering information of menstruation of a woman into a data server which is connected with a network server of the internet via different terminals which are connected with the internet;
2. establishing a data base about the menstruation information of the woman in the data server depending on the entered information;
3. calculating the ovulation day, the impregnable days, and the starting day of a following menstruation of the woman in the network server; and
4. sending out inquired forecast information to the woman via the different terminals.

Figure 1:
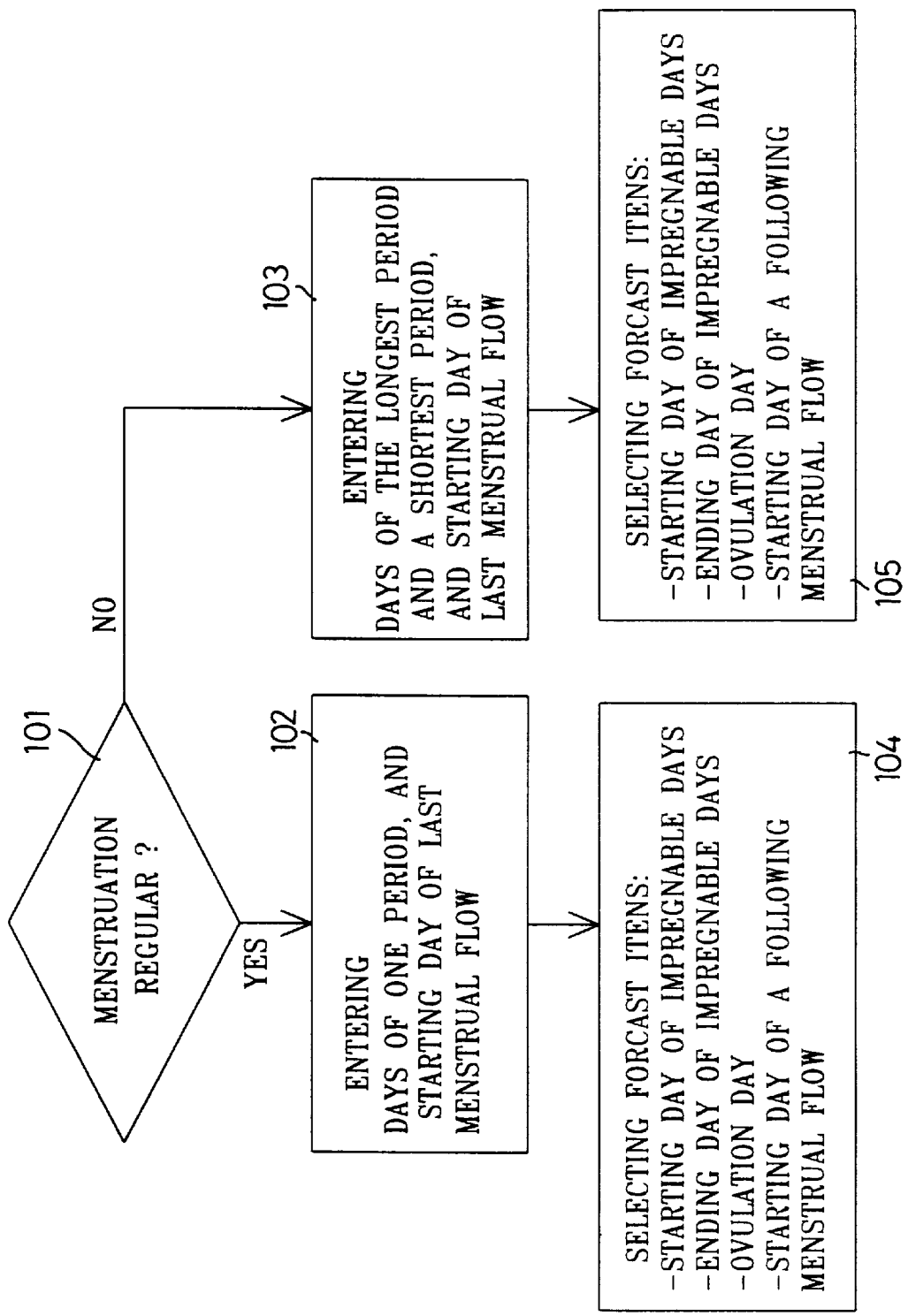
FIG. 1 is a flow chart of establishing a data base in a forecasting system in accordance with the present invention.

The terminal may be a mobile telephone which supports WAP or a personal computer which is capable of connecting with the internet. As shown in FIG. 1, the forecasting system first goes to a step 101 to ask the woman "Is your menstruation regular?" Next, if the woman inputs "Yes", the system goes to a step 102 to tell the woman "Input starting day of a last menstrual flow and total days of one period". If the woman inputs "No", the system goes to a step 103 to tell the, woman to "Input starting day of a last menstruation, total days of a shortest period and total days of a longest period". Afterwards, the system goes to a step 104 to ask the woman "Which items do you want to be forecasted: starting day of impregnable days; ending day of impregnable days; ovulation day; starting day of a following menstrual flow?" The forecast system establishes a data base for the woman in the data server depending on the information entered by the woman.

Figure 2:
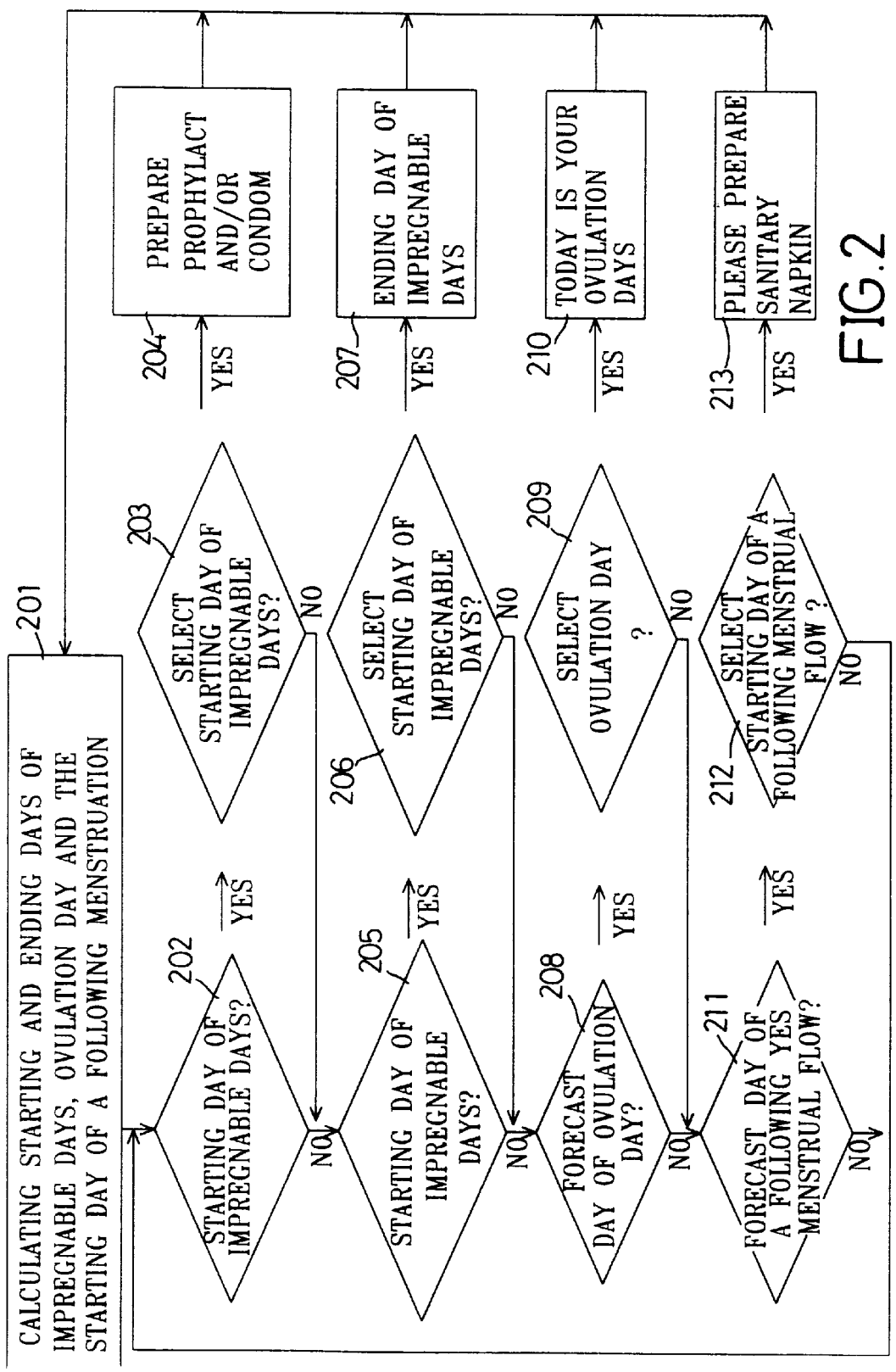
FIG. 2 is a flow chart of forecasting different times of a following period by the forecasting system in accordance with the present invention.

As shown in FIG. 2, first the forecasting system runs a step 201 to calculate the ovulation day, the starting day of impregnable days, the ending day of impregnable days and the starting day of a following menstrual flow depending on the information of the data base established in the data server.

There are formulas for regular menstruation:
ovulation day=starting day of a last menstrual flow plus total days of one period less 14;
starting day of impregnable days=ovulation day less 3;
ending day of impregnable days=ovulation day plus 3;
starting day of a following menstrual flow=starting day of a last menstrual flow plus total days of one period.
And there are formulas for irregular menstruation:
average total days of menstruation=average of the shortest and the longest period;
ovulation day=starting day of a last menstrual flow plus average total days of menstruation less 14;
starting day of impregnable days=total days of a shortest period less 18;
ending day of impregnable days=total days of a longest period less 11;
starting day of a following menstrual flow=starting day of the last menstrual flow plus average total days of menstruation.

Next the forecasting system goes to a step 202 to ask "Is today is a forecast day of a starting day of impregnable days?" If it is, then the system goes to a step 203. If it is not, then the system goes to a step 205. The step 203 asks "Has forecasting a starting day of impregnable days been selected by the woman?" If it has, then the system goes to a step 204. If it has not, then the system goes to the step 205. The step 204 sends out an E-mail, "Please prepare prophylactic and/or condom" to a mail address of the woman, and afterwards the system returns to the step 201.

The step 205 asks "Is today is a forecast day of ending day of impregnable days?" If it is, then the system goes to a step 206. If it is not, then the system goes to a step 208. The step 206 asks "Has forecasting an ending day of impregnable days been selected by the woman?" If it has, then the system goes to a step 207. If it is not, then the system goes to the step 208. The step 207 sends out an E-mail, "Today is your ending day of impregnable days" to the mail address of the woman, and afterwards the system returns to the step 201.

The step 208 asks "Is today a forecast ovulation day?" If it is, then the system goes to a step 209. If it is not, then the system goes to a step 211. The step 209 asks "Has forecasting the ovulation day been selected by the woman". If it has, then the system goes to a step 210. If it has not, then the system goes to the step 211. The step 210 sends out an E-mail, "Today is your ovulation day" to the mail address of the woman, and afterwards the system returns to the step 201.

The step 211 asks "Is today a forecast starting day of a following menstrual flow?" If it is, then the system goes to a step 212. If it is not, then the system returns to a step 202. The step 212 asks "Has forecasting the starting day of a following menstrual flow been selected by the woman?" If it has, then the system goes to a step 213. If it has not, then the system returns to the step 202. The step 213 sends out an E-mail, "Please prepare sanitary napkins" to the mail address of the woman, and afterwards the system returns to the step 201.

Figure 3:
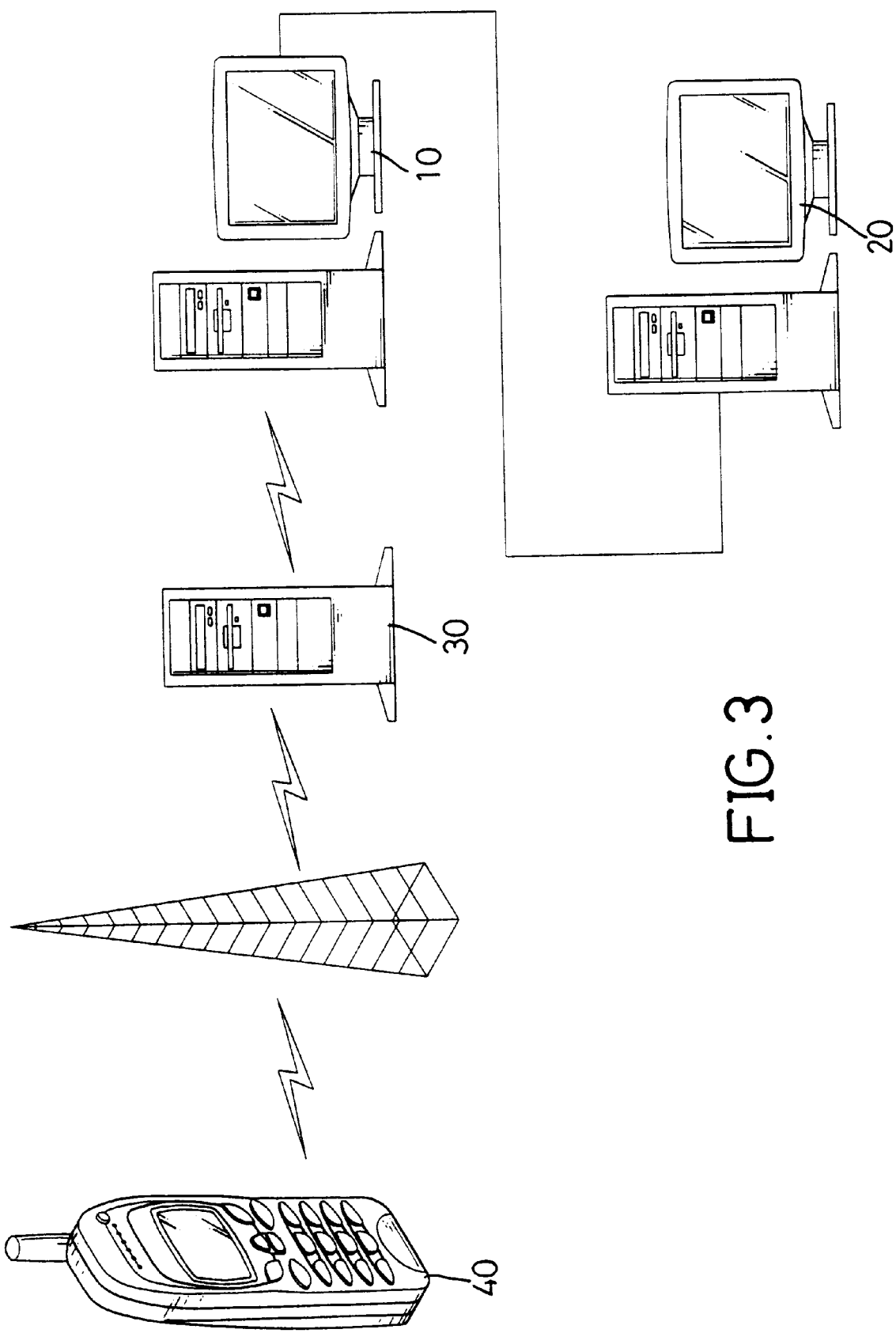
FIG. 3 is a schematic view of a first embodiment of a terminal of the forecasting system in accordance with the present invention, wherein the terminal is connected with a mobile telephone supporting WAP.

Forecasts sent out from the network server are received by the woman via different terminals. A first embodiment is shown in FIG. 3, a network server (10) is connected with a data server (20). The data server (20) is used to save data of information therein. The network server (10) is used to communicate with terminals. A communication gateway (30) is serviced between the network server (10) and a mobile telephone (40) which supports WAP, whereby a user is able to get access onto the internet via the mobile telephone (40). When the user has connected with the internet via the mobile telephone (40), the user can enter relative information into the data server (20) via the mobile telephone (40), and receive a forecast sent out from the network server (10) via the mobile telephone (40).

Figure 4:
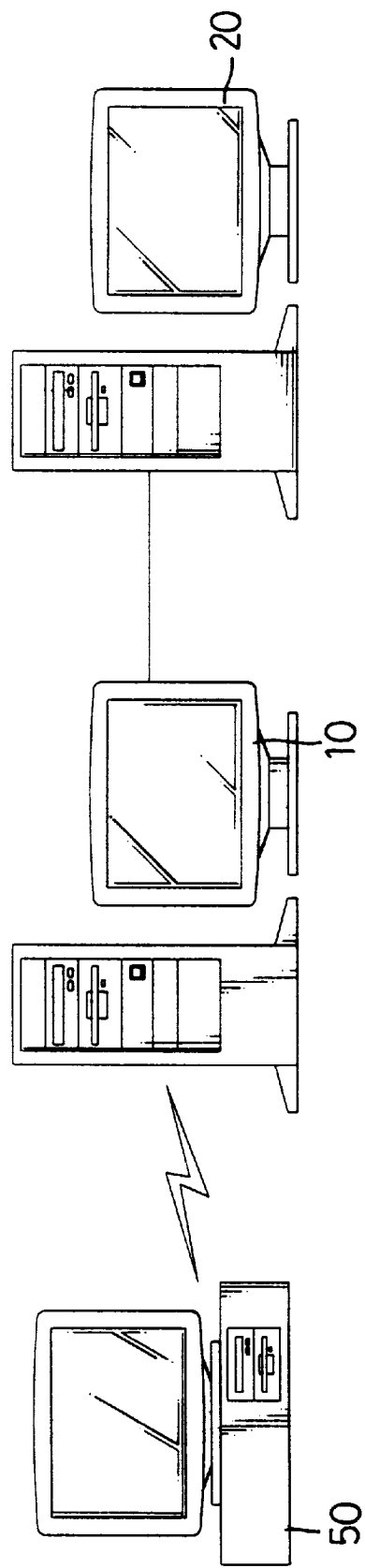
FIG. 4 is a schematic view of a second embodiment of the terminal of the forecasting system in accordance with the present invention, showing a computer is connected with the E-mail system.

A second embodiment is shown in FIG. 4, a network server (10') is connected with a data server (20'). When a user gets access onto the internet via a personal computer (50), the user can enter relative information into the data server (20') via the personal computer (50), and receive a forecast from the network server (10) via the personal computer (50).

The above described forecasting system is simple and easily operable, which assists women who want to organize their lives or working plans smoothly and give up the trouble of remembering the starting day of a last menstruation by rote.

It is to be understood, however, that even though numerous characteristics and advantages of the present invention have been set forth in the foregoing description, together with details of the structure and function of the invention,: the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A forecast method for menstruation of women, which method includes:

entering information about menstruation of a woman into a, data server which is connected with a network server of the internet via a terminal which is connected with the internet;

establishing a data base about the menstruation information of the woman in the data server, the data base depending on the entered information;

calculating the ovulating day, the impregnable days, and the starting day of a following menstruation of the woman in the network server; and sending out inquired forecast information to the woman via the terminal;

wherein the entering of information includes:
determining whether the woman's menstruation is regular;
requiring input of a starting day of a last menstruation and total days of one period, if the response to whether the woman's menstruation is regular is positive;
requiring input of a starting day of a last menstruation, total days of a longest period, and total days of a shortest period, if the response to whether the woman's menstruation is regular is negative; and
requiring input of which items are to be forecasted.

2. The forecasting method for menstruation of women as claimed in claim 1, wherein calculation formulas for regular menstruation comprise:

ovulation day=starting day of a last menstrual flow plus total days of one period less 14;

starting day of impregnable days=ovulating day less 3;

ending day of impregnable days=ovulating day plus 3; and starting day of a following menstrual flow=starting day of a last menstrual flow plus total days of one period.

3. The forecasting method for menstruation of women as claimed in claim 1, wherein calculation formulas for irregular menstruation comprise:

average total days of menstruation=average of the shortest and the longest period;

ovulation day=starting day of a last menstrual flow plus total days of one period less 14;

starting day of impregnable days=total days of a shortest period less 18;

ending day of impregnable days=total days of a longest period less 11; and starting day of a following menstrual flow=starting day of a last menstrual flow plus average total days of menstruation.

4. The forecasting method for menstruation of women as claimed in claim 1, wherein the system includes, as selectable forecast items:

starting day of impregnable days;

ending day of impregnable days; and ovulation and starting day of a following menstrual flow.

5. The forecasting method for menstruation of women as claimed in claim 1, wherein the terminal is a mobile telephone which is capable of connecting with the internet.

6. The forecasting method for menstruation of women as claimed in claim 5, wherein the mobile telephone supports WAP.

7. The forecasting method for menstruation of women as claimed in claim 1, wherein the terminal is a personal computer which is capable of connecting with the internet.

\* \* \* \* \*